(12) United States Patent
Gaignet

(10) Patent No.: US 7,057,400 B2
(45) Date of Patent: Jun. 6, 2006

(54) FLUID CONDUCTIVITY MEASURING CELL

(75) Inventor: Yves Gaignet, Montigny le Bretonneux (FR)

(73) Assignee: Millipore Corporation, Billerica, MA (US)

( * ) Notice: Subject to any disclaimer, the term of this patent is extended or adjusted under 35 U.S.C. 154(b) by 0 days.

(21) Appl. No.: 11/116,737

(22) Filed: Apr. 28, 2005

(65) Prior Publication Data

US 2005/0258839 A1 Nov. 24, 2005

(30) Foreign Application Priority Data

May 17, 2004 (FR) .................................. 04 05347

(51) Int. Cl.
*G01R 27/08* (2006.01)

(52) U.S. Cl. ....................... 324/696; 324/449

(58) Field of Classification Search ...................... None
See application file for complete search history.

(56) References Cited

U.S. PATENT DOCUMENTS 4,767,995 A * 8/1988 Berry, Jr. .................... 324/447

5,973,503 A * 10/1999 Kuipers et al. ............. 324/698

FOREIGN PATENT DOCUMENTS

EP 0498888 A1 8/1992
GB 2196202 A 4/1988

* cited by examiner

*Primary Examiner*—Vincent Q. Nguyen
(74) *Attorney, Agent, or Firm*—Millipore Corporation

(57) ABSTRACT

The invention relates to a fluid conductivity measuring cell having two cylindrical and coaxial electrodes mounted head-to-tail and axially overlapping on the same insulative body, the inner electrode, penetrating partly into the at least partly hollow outer electrode has a recess in which the two electrodes are accommodated to form two cylindrical spaces, one of which is an external space formed between the internal wall of the recess and the external wall of the outer electrode and the other being an internal space formed between the external wall of the inner electrode and the internal wall of the outer electrode, the external space establishing communication between a fluid inlet and a fluid outlet of the cell, each discharging into the recess and being in fluid communication with the internal space that is surrounds, this internal space serving as a conductivity measuring area.

21 Claims, 2 Drawing Sheets

FLUID CONDUCTIVITY MEASURING CELL

CROSS REFERENCE RELATED APPLICATIONS

Figure 1:
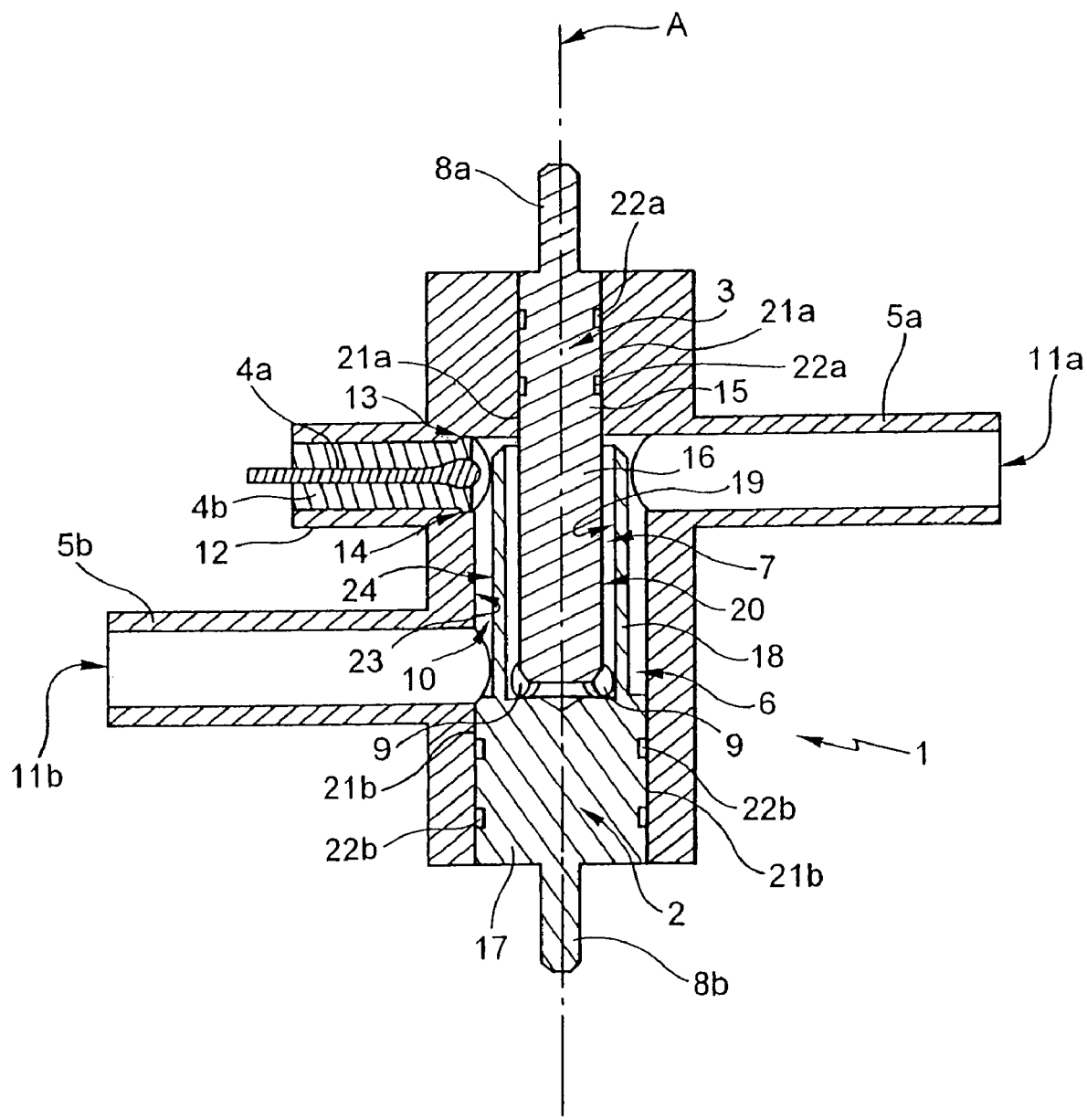

This application claims priority to French Application No.: 0405347, filed on May 17, 2004.

The present invention relates to the field of determining the purity of water by measuring its conductivity or resistivity (resistivity in ohm.cm=1/conductivity in Siemens.cm$^{-1}$) and in particular to a conductivity cell with thermal compensation and axially overlapping coaxial cylindrical electrodes that may be fitted to a water line whose purity is to be determined. However, the invention applies equally to measuring the conductivity of any other fluid.

Many modern technological applications require pure or ultrapure water for their operation, in particular in the chemical, pharmaceutical, medical and electronic industries.

Quite apart from problems associated with water purification, it is necessary to improve the performance of instrumentation for measuring the quality of purified water.

A conductivity cell is a device for determining the ionic purity of water. This type of cell advantageously uses one of the properties of water, namely the fact that its conductivity is proportional to the concentration of ions that it contains. As the purity of water increases, its conductivity decreases and its resistivity increases. Accordingly, to measure the conductivity of water, the electrical resistance between two spaced conductive surfaces immersed in the water whose purity is to be determined may be measured. Knowing the geometry of the surfaces and that of the space between them, it is possible to deduce from the measured value of the resistance, the conductivity of the water and therefore its concentration of ions, and thereby to determine its purity.

The measured electrical resistance of the water depends on the geometry of the surfaces and the distance between the electrodes, which together define the cell constant (cell constant=distance in cm/area in cm$^2$). The lower the cell constant, the greater the accuracy of the measured conductivity of the pure or ultrapure water. A constant from 0.1 to 0.01 is recommended by the international standards for this application.

It is therefore beneficial to minimize this constant. There are two options in the case of cells with coaxial and axially overlapping cylindrical electrodes:

- to increase the area of the electrodes (i.e. the length and/or diameter of the electrodes), or
- to reduce the gap between the interior electrode and the exterior electrode.

For low water flowrates it is preferable to use small cells, and thus in this case the first of the above two options is not recommended.

Consequently, to increase the accuracy of a coaxial cell with cylindrical electrodes, an attempt must be made to reduce the space between the electrodes. The measured resistance of the water contained between the electrodes as a function of the ratio between the outside diameter of the inner electrode and the inside diameter of the outer electrode obeys a logarithmic law. The farther apart the electrodes, the higher the cell constant and thus the less accurate the measurement.

Given the logarithmic nature of this law, it is beneficial not only to reduce the distance between the two electrodes, and thus the cell constant, but also, and more importantly, in the context of mass production, to design the cell so that all the cells manufactured have a similar cell constant; existing cells satisfy the above criteria only in part.

Furthermore, pure or ultrapure water has a very high resistivity that is strongly affected by the temperature of the water. Measuring the conductivity corresponding to this resistivity necessitates a knowledge of the temperature of the water at the time of the analysis if a precise result is to be obtained. Conductivity measuring cells therefore generally contain a temperature sensor in addition to the electrodes.

The sensor must be positioned to obtain a short response time in order for the electrical resistance measured between the two electrodes at a precise time to correspond to the temperature measured by said sensor at the same time.

Moreover, most conductivity cells are designed to be mounted directly in a water line in order to determine the conductivity of the water practically continuously.

This causes two major problems that at present are only partly solved, namely "dead areas" and head losses.

In some cells there are areas in which water stagnates ("dead areas"), caused for example by mounting the cell in a Tee, especially in the measuring area between the electrodes. The resistivity is therefore not measured in "fresh" water but in water that has stagnated in the cell, which is therefore not representative of the real resistivity of the water flowing through the cell. It is therefore important to design the space between the two electrodes to avoid any stagnation of water there.

Depending on the construction of the cell, greater or lesser head losses (pressure drops) are also observed between the inlet and the outlet of the cell when installed in a water line. Like any measuring instrument, the cell interferes with its environment. It is therefore necessary to limit its effects in order not to degrade the performance of the water line, especially if it was designed to operate without the cell.

Existing technology provides no means of accurately controlling the pressure drops and the turbulence of the water caused by its passage through the cell, in particular because all of the water passing through the cell passes between the two electrodes.

Further, existing cells are very often of complex construction and assembly in that they must integrate the various constraints previously cited, which imposes the use of seals, threaded fixings and additional centering bearing surfaces to position the electrodes accurately, which increases their unit cost and assembly time.

The device from the document GB 2 210 459 uses O-rings not only as seals but also to center the inner electrode relative to the outer electrode. From the mechanical design point of view, an O-ring is unable to provide a centering function correctly, especially if the accuracy of the latter function affects the cell constant and therefore the performance of the cell. Moreover, the use of seals and machined threads increases the production cost of the cell.

U.S. Pat. No. 4,767,995 discloses a conductivity measuring cell that is adjustable to enable it to adapt to various measurement orders of magnitude. The adjustment is effected by means of a threaded rod which moves the inner cylindrical electrode in translation in a bore in order to penetrate farther or less far into the outer electrode. Because of its design, this cell cannot provide sufficient reliability of the cell constant between two measurements, as it is difficult to return the inner electrode to exactly the same position relative to the outer electrode. Measurements effected with this type of cell are less accurate than those effected using non-adjustable cells. Moreover, this cell employs a large number of complex components necessitating machining, fitting, external threads, internal threads, and seals for moving parts, and is consequently costly to produce.

Finally, like the previous two documents, U.S. Pat. No. 3,916,300 discloses a cell with concentric cylindrical electrodes assembled by screwed-on covers and centered by parts attached and fitted to the electrodes, which increases its cost for the reasons previously cited.

Finally, it will be noted that in the three documents cited all of the water entering the cell passes between the two electrodes, which creates head losses that are problematic when the cell is installed on a water line. In this regard, it should be noted that in these three cases the design choice appears to have been dictated by the desire to avoid the introduction of "dead areas".

The invention aims to alleviate the drawbacks of the prior art previously cited.

A general object of the invention is a fluid conductivity measuring cell adapted to be fitted to a circulation line for said fluid and comprising two cylindrical and coaxial electrodes mounted head-to-tail and axially overlapping on the same insulative material component body, one of the two electrodes, referred to as the inner electrode, penetrating partly into the other, at least partly hollow electrode, referred to as the outer electrode, which cell is characterized in that the body comprises a recess by means of which the two electrodes are accommodated in such a manner as to form two cylindrical spaces, one of which is an external space formed between the internal wall of the recess and the external wall of the external electrode and the other of which is an internal space formed between the external wall of the internal electrode and the internal wall of the external electrode, the external space establishing communication between a fluid inlet and a fluid outlet of the cell, each discharging into the recess and being in fluid communication with the internal space that it surrounds, this internal space serving as a conductivity measuring area.

According to preferred and where applicable combinable features of the invention:
  the electrodes are force-fitted into the recess in the body which is open to the outside at each end;
  the anchorage between the electrodes and the body is provided by at least one triangular profile collar provided on an anchoring section of each of the electrodes;
  the anchoring section of each of the electrodes comprises a groove parallel to the collar;
  the external electrode has, at the blind end of a hollow measuring section forming the external wall of the internal space and extending the anchoring section of the external electrode, openings enabling the measuring section to communicate with the external space;
  a cavity, which is preferably open to the outside of the cell, is provided in the body in such a manner that it is possible to accommodate therein a temperature sensor adapted to come into contact with the fluid whose conductivity is to be measured, or the internal electrode is hollow in order to be able to accommodate a temperature sensor therein;
  the sensor is carried by a support preferably having a shoulder adapted to cooperate with a complementary shoulder of the body to retain the sensor to the body;
  the temperature sensor is of the thermistor or platinum probe type;
  the support takes the form of a protective glove finger for the sensor;
  the fluid inlet is at one longitudinal end of the measuring section of the external electrode and the fluid outlet is at the opposite end of the measuring section;
  the fluid inlet and outlet are angularly spaced, preferably at 180°;
  the internal electrode is a solid electrode;
  the fluid inlets and outlets and the cavity housing the sensor are formed in appendices extending transversely to an axis of the recess;
  the electrodes comprise identical electrical connection terminals.

The particularity of this invention is that it yields a cell in which the two electrodes are force-fitted in a head-to-tail arrangement into the same insulative material body, in which the two spaces provided for the electrodes are molded (and/or machined) on the same spindle, to guarantee excellent concentricity of the two electrodes once mounted in said body.

More generally, only a portion of the fluid entering the cell is used to measure the conductivity, the remainder being fed directly to the outlet of the cell.

To this end, the cell is designed to have two spaces inside the body, one causing the fluid to pass between the two electrodes in the head-to-tail position and serving the conductivity measuring area, and the other lying between the body and the outer electrode, to feed the greater portion of the liquid directly to the outlet, without passing through the first space.

Moreover, the electrodes may each be provided at their exterior anchorage ends (the ends adapted to be inserted into the body of the cell) with collars barbed like a harpoon, to guarantee sealing and retention of the electrodes relative to the body, even in the event of a high fluid pressure inside the cell.

Thus the cell has the advantage that no seals are required to seal it.

The temperature of the fluid is measured by a thermistor or a platinum probe mounted either in a cavity in the body of the cell, inside the inner electrode, which is pierced for this purpose and serves as a protective glove finger, or in an attached glove finger that is preferably crimped on.

The temperature probe may also be mounted in an elastomer member nested in an orifice in the cell body. This elastomer member then serves as a member for fixing and sealing the probe relative to the cell body and allows the head of the probe to be in direct contact with the fluid, which improves the response time of the probe.

The electrodes are advantageously force-fitted into molded spaces that are molded with the same spindle, which ensures very accurate relative positioning of the two electrodes and achieves a low and accurate cell constant in the context of mass production. The tight fit between said spaces and the electrodes guarantees that the cell is sealed.

Moreover, using only a portion of the fluid passing through the cell for the measurement reduces head losses and makes the cell adaptable to different applications (pressures, flowrates, etc.), in particular by modifying the geometry of the members constituting its internal passages (central cavity of the body, electrodes, geometry of the two internal spaces, etc.).

By the simplicity of its construction, the present cell is very economic, as it has only few components, i.e. four main subassemblies (a body, two electrodes and a temperature measuring unit). Its clever design means that it may be assembled quickly, without seals and without adjustments, and this contributes greatly to reducing the unit cost of this type of cell.

Moreover, the triangular profile collar holds the electrodes in place even if high pressures are exerted inside the cell.

The invention also relates to a device for transporting, treating or controlling a fluid, characterized in that it comprises a conductivity measuring cell as defined above.

It may be a fluid control manifold, for example, a casing containing a reverse osmosis or similar cartridge, or a water treatment equipment component.

The body of the cell is preferably in one piece with the device, being very simply molded in one and the same piece therewith, which is to the benefit of costs.

Finally, the temperature sensor may be placed in direct contact with the fluid to achieve an optimum response time and thereby improve measurement accuracy.

Figure 2:
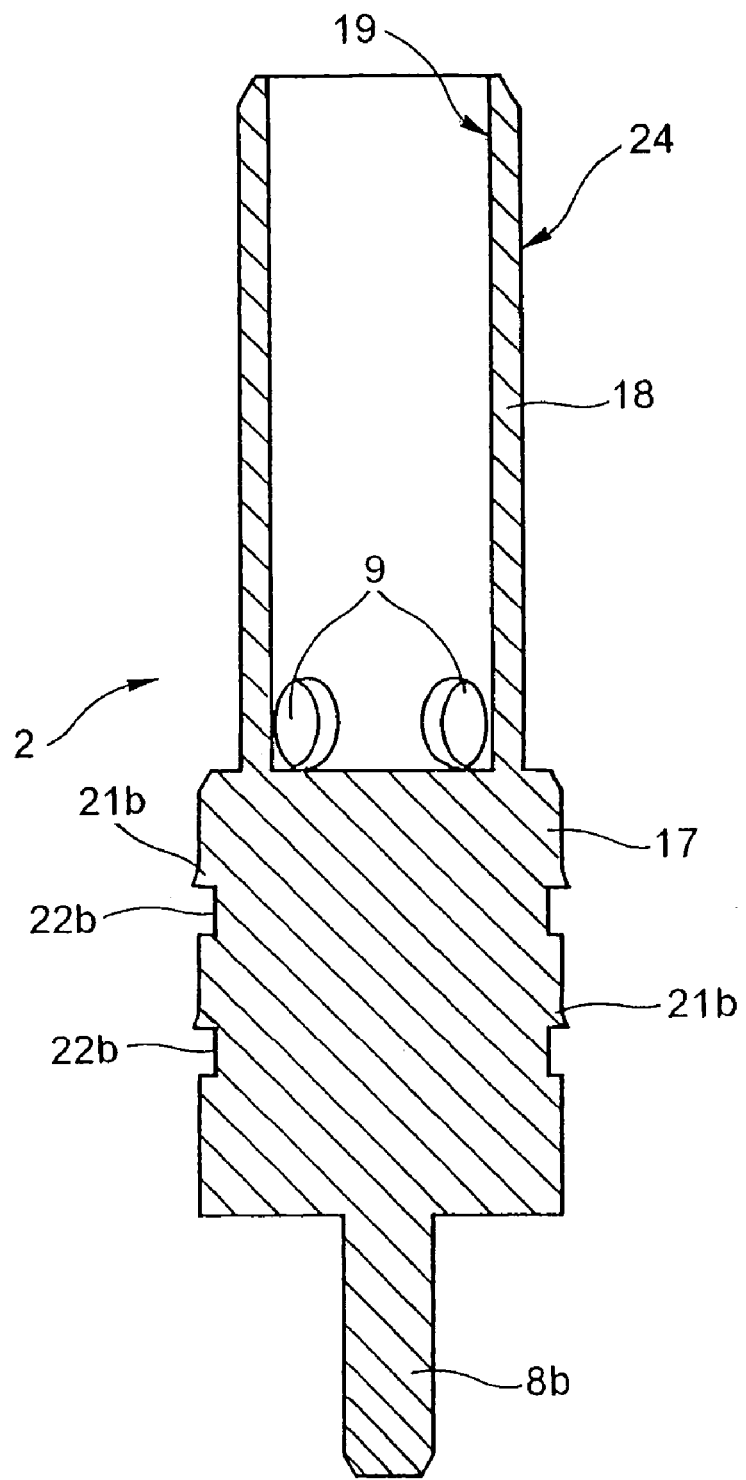

Other advantages of the present invention will become apparent on reading the following description with reference to the drawings, in which:

FIG. 1 is a view in section of a preferred embodiment of a conductivity measuring cell of the invention, and FIG. 2 is a view in section and to a larger scale of the outer electrode of the FIG. 1 cell.

It should be noted at this point that the following description is that of a preferred embodiment and is given by way of nonlimiting example.

The conductivity measuring cell represented in FIG. 1 comprises a molded insulative material cylindrical body 1 that integrates a plurality of hydraulic and mechanical functions and comprises a massive hollow central part and three hollow cylindrical appendices transverse its axis and opening into the central part.

To be more precise, the body 1 has a cylindrical longitudinal central passage 10 with axis A and of varying diameter that passes completely through it. This passage 10 is produced using the same spindle when molding the body, which ensures that the electrodes, once fitted, are concentric. The body 1 is designed for the two electrodes to be mounted in a head-to-tail arrangement.

On respective opposite sides of the central passage 10 the cell body has two orifices 11a and 11b spaced in the longitudinal direction of the body 1 and angularly spaced with respect to each other, here at 180°. Each of the orifices 11a and 11b discharges into a respective hydraulic pipe 5a and 5b, each of which forms an appendix projecting radially from the body 1 and opening into the central passage 10 at the end opposite the end 11a or 11b intended to constitute either the inlet or the outlet for the fluid to be analyzed.

Moreover, diametrically opposite the orifice 11a is a third hollow cylindrical appendix 12 projecting radially from the body 1 and designed for installing in the body 1 a temperature sensor 4a, here of the thermistor type, and its support 4b.

The cell further comprises two coaxial cylindrical electrodes: a solid electrode 3 and a hollow electrode 2. The solid electrode 3 comprises a connection terminal 8a, an anchor section 15 and a measuring section 16, these sections being solid and of exactly the same diameter; the other electrode 2 also comprises a connection terminal 8b and a solid anchor section 17, but its measuring section 18, of smaller outside diameter than its anchor section 17, is hollow, the inside diameter of this hollow portion being greater than the outside diameter of the solid electrode 3, so that the latter may be partially accommodated inside the electrode 2, in the longitudinal direction.

The electrodes 2 and 3 are machined from a conductive material and designed to be force-fitted into their locations in the body, to provide a perfect seal and perfect centering of the electrodes. Each of the two electrodes 2, 3 has for this purpose, and as seen better in FIG. 2, on their anchor section intended to come into contact with the body 1, two triangular profile collars 21a, 21b designed to anchor the electrodes in position, especially in the event of a high fluid pressure inside the cell, and each delimited longitudinally by a groove 22a, 22b parallel to the associated collar, to produce a sharper edge of the collar, improving its anchoring and allowing the insulative material to flow into the groove.

The hollow section 18 of the outer electrode 2 surrounds substantially all of the free (unanchored) portion of the inner electrode 3 lying inside the central passage 10, to form a conductivity measuring space 7.

As indicated above, the outer electrode 2 is to this end hollow at the center to provide a passage for the inner electrode 3 and create said space 7.

For the latter not to be a "dead area", holes 9 are provided at the base of the hollow portion (at the closed end of the measuring section 18) of the outer electrode 2 to improve the circulation of fluid in said space 7.

Fluid entering the probe through one of the hydraulic connections 5a, 5b is therefore shared between:

the conductivity measuring space 7 between the two electrodes 2 and 3 (between the internal wall 19 of the outer electrode 2 and the external wall 20 of the inner electrode 3), and the free space 6 between the outer electrode 2 and the body of the cell 1 (between the internal wall 23 of the hollow portion 10 and the external wall 24 of the outer electrode 2), which surrounds the space 7, communicates therewith, and establishes communication between the fluid inlets and outlets 11a/11b of the cell.

This minimizes or even eliminates head losses.

The temperature probe 4a is installed in an elastomer support 4b that is a tight fit in the passage 12 provided for this purpose in the body 1.

The support 4b has at one end a shoulder 14 that prevents separation of said support 4b and the body 1, in particular in the event of a high fluid pressure inside the cell, through cooperation with a complementary shoulder 13 formed on the body.

It will also be noted that the electrodes 2, 3 have connection terminals 8 of identical shape which project from the body 1 when the electrodes are fitted, to standardize their electrical connections.

In a different embodiment, fabricating the body 1 by a machining process could be envisaged.

In another embodiment, fabricating the electrodes 2 and 3 by precision molding could be envisaged.

The space between the outer electrode 2 and the body of the probe 1 may differ from one design of cell to another to suit the fluid flowrate through it.

The geometry of the electrodes (diameter, length and distance between the electrodes) may also be modified as a function of the conductivity of the fluid to be measured.

More generally, the present invention is not limited to the embodiment described and shown, but encompasses any variant execution thereof.

The invention claimed is:

1. A fluid conductivity measuring cell adapted to be fitted to a circulation line for said fluid and comprising an insulative material component body, two cylindrical and coaxial electrodes mounted head-to-tail and axially overlapping on the same insulative material component body, one of the two electrodes, referred to as the inner electrode, penetrating partly into the other, at least partly hollow electrode, referred to as the outer electrode, which cell is characterized in that the body comprises a recess by means of which the two electrodes are accommodated in such a manner as to form two cylindrical spaces, one of which is an external space formed between an internal wall of the recess and external wall of the outer electrode and the other of which is an internal space formed between an external wall of the inner electrode and an internal wall of the electrode, the external space establishing communication between a fluid inlet and a fluid outlet of the cell, each discharging into the recess and being in fluid communication with the internal space that it surrounds, this internal space serving as a conductivity measuring area.

2. A cell according to claim 1, characterized in that the electrodes are anchored to the body and the anchorage between the electrodes and the body is provided by at least one triangular profile collar provided on an anchoring section of each of the electrodes and the anchoring section of each of the electrodes comprises a grove parallel to the collar.

3. A cell according to claim 1, characterized in that a cavity which is preferably open to the outside of the cell, is provided in the body in such a manner that it is possible to accommodate therein a temperature sensor adapted to come into contact with the fluid whose conductivity is to be measured, or the inner electrode is hollow in order to be able to accommodate a temperature sensor therein and the sensor is carried by a support preferably having a shoulder adapted to cooperate with a complementary shoulder of the body to retain the sensor to the body.

4. A cell according to claim 1 further comprising a temperature sensor mounted within the body and adapted to come into contact with the fluid whose conductivity is to be measured and the temperature sensor is of the thermistor or platinum probe type.

5. A cell according to claim 1, characterized in the fluid inlet is at one longitudinal end of the measuring section of the outer electrode and the fluid outlet is at the opposite end of the measuring section.

6. A cell according to claim 1, characterized in that the fluid inlet and outlet are angularly spaced, preferably at 180°.

7. A cell according to claim 1, characterized in that the inner electrode is a solid electrode.

8. A cell according to claim 1, characterized in that the fluid inlet and outlet are formed in appendices extending transversely to an axis of the recess.

9. A cell according to claim 1, characterized in that the electrodes comprise identical electrical connection terminals.

10. A device for transporting, treating or controlling a fluid, characterized in that it comprises a conductivity measuring cell according to claim 1.

11. A device for transporting, treating or controlling a fluid, characterized in that it comprises a conductivity measuring cell according to claim 1, characterized in that the body of the conductivity measuring cell is in one piece with the device.

12. A cell according to claim 1, further comprising a cavity within the body for housing a sensor and wherein the fluid inlet, fluid outlet and cavity are formed in appendices extending transversely to an axis of the recess.

13. A fluid conductivity measuring cell adapted to be fitted to a circulation line for said fluid and comprising an insulative material component body, two cylindrical and coaxial electrodes mounted head-to-tail and axially overlapping on the same insulative material component body, one of the two electrodes, referred to as the inner electrode, penetrating partly into the other, at least partly hollow electrode, referred to as the outer electrode, which cell is characterized in that the body comprises a recess by means of which the two electrodes are accommodated in such a manner as to form two cylindrical spaces, one of which is an external space formed between an internal wall of the recess and an external wall of the outer electrode and the other of which is an internal space formed between an external wall of the inner electrode and an internal wall of the electrode, the external space establishing communication between a fluid inlet and a fluid outlet of the cell, each discharging into the recess and being in fluid communication with the internal space that it surrounds, this internal space serving as a conductivity measuring area and wherein the electrodes are forced-fitted into the recess in the body which is open to the outside at each end.

14. A fluid conductivity measuring cell adapted to be fitted to a circulation line for said fluid and comprising an insulative material component body, two cylindrical and coaxial electrodes mounted head-to-tail and axially overlapping on the same insulative material component body, one of the two electrodes, referred to as the inner electrode, penetrating partly into the other, at least partly hollow electrode, referred to as the outer electrode, which cell is characterized in that the body comprises a recess by means of which the two electrodes are accommodated in such a manner as to form two cylindrical spaces, one of which is an external space formed between an internal wall of the recess and an external wall of the outer electrode and the other of which is an internal space formed between an external wall of the inner electrode and an internal wall of the electrode, the external space establishing communication between a fluid inlet and a fluid outlet of the cell, each discharging into the recess and being in fluid communication with the internal space that it surrounds, this internal space serving as a conductivity measuring area and wherein the electrodes are anchored to the body and the anchorage between the electrodes and the body is provided by at least one triangular profile collar provided on an anchoring section of each of the electrodes.

15. A cell according to claim 14, characterized in that the anchoring section of each of the electrodes comprises a grove parallel to the collar.

16. A fluid conductivity measuring cell adapted to be fitted to a circulation line for said fluid and comprising an insulative material component body, two cylindrical and coaxial electrodes mounted head-to-tail and axially overlapping on the same insulative material component body, one of the two electrodes, referred to as the inner electrode, penetrating partly into the other, at least partly hollow electrode, referred to as the outer electrode, which cell is characterized in that the body section forming the external wall of the internal space and extending the anchoring comprises a recess by means of which the two electrodes are accommodated in such a manner as to form two cylindrical spaces, one of which is an external space formed between an internal wall of the recess and an external wall of the outer electrode and the other of which is an internal space formed between an external wall of the inner electrode and an internal wall of the electrode, the external space establishing communication between a fluid inlet and a fluid outlet of the cell, each discharging into the recess and being in fluid communication with the internal space that it surrounds, this internal space serving as a conductivity measuring area and wherein the outer electrode is anchored to the body and the outer electrode has, at a blind end of a hollow measuring section of the outer electrode, openings enabling the measuring section to communicate with the external space.

17. A fluid conductivity measuring cell adapted to be fitted to a circulation line for said fluid and comprising an insulative material component body, two cylindrical and coaxial electrodes mounted head-to-tail and axially overlapping on the same insulative material component body, one of the two electrodes, referred to as the inner electrode, penetrating partly into the other, at least partly hollow electrode, referred to as the outer electrode, which cell is characterized in that the body comprises a recess by means of which the two electrodes are accommodated in such a manner as to form two cylindrical spaces, one of which is an external space formed between an internal wall of the recess and an external wall of the outer electrode and the other of which is an internal space formed between an external wall of the inner electrode and an internal wall of the electrode, the external space establishing communication between a fluid inlet and a fluid outlet of the cell, each discharging into the recess and being in fluid communication with the internal space that it surrounds, this internal space serving as a conductivity measuring area and further comprising a cavity, which is preferably open to the outside of the cell, is provided in the body in such a manner that it is possible to accommodate therein a temperature sensor adapted to come into contact with the fluid whose conductivity is to be measured, or the inner electrode is hollow in order to be able to accommodate a temperature sensor therein.

18. A cell according to claim 17 wherein the temperature sensor is carried by a support preferably having a shoulder adapted to cooperate with a complementary shoulder of the body to retain the sensor to the body.

19. A cell according to claim 17 wherein the temperature sensor is selected from the group consisting of the thermistor and platinum probe type sensors.

20. A fluid conductivity measuring cell adapted to be fitted to a circulation line for said fluid and comprising an insulative material component body, two cylindrical and coaxial electrodes mounted head-to-tail and axially overlapping on the same insulative material component body, one of the two electrodes, referred to as the inner electrode, penetrating partly into the other, at least partly hollow electrode, referred to as the outer electrode, which cell is characterized in that the body comprises a recess by means of which the two electrodes are accommodated in such a manner as to form two cylindrical spaces, one of which is an external space formed between an internal wall of the recess and an external wall of the outer electrode and the other of which is an internal space formed between an external wall of the inner electrode and an internal wall of the electrode, the external space establishing communication between a fluid inlet and a fluid outlet of the cell, each discharging into the recess and being in fluid communication with the internal space that it surrounds, this internal space serving as a conductivity measuring area and further comprising a temperature sensor mounted within the body and adapted to come into contact with the fluid whose conductivity is to be measured and the temperature sensor is selected from the group consisting of the thermistor and platinum probe type sensors.

21. A fluid conductivity measuring cell adapted to be fitted to a circulation line for said fluid and comprising an insulative material component body, two cylindrical and coaxial electrodes mounted head-to-tail and axially overlapping on the same insulative material component body, one of the two electrodes, referred to as the inner electrode, penetrating partly into the other, at least partly hollow electrode, referred to as the outer electrode, which cell is characterized in that the body comprises a recess by means of which the two electrodes are accommodated in such a manner as to form two cylindrical spaces, one of which is an external space formed between an internal wall of the recess and an external wall of the outer electrode and the other of which is an internal space formed between an external wall of the inner electrode and an internal wall of the electrode, the external space establishing communication between a fluid inlet and a fluid outlet of the cell, each discharging into the recess and being in fluid communication with the internal space that it surrounds, this internal space serving as a conductivity measuring area and further comprising a temperature sensor mounted within the body and adapted to come into contact with the fluid whose conductivity is to be measured, the sensor is carried by a support preferably having a shoulder adapted to cooperate with a complementary shoulder of the body to retain the sensor to the body and the support takes the form of a protective glove finger for the sensor.

* * * * *